United States Patent
Heglund et al.

(10) Patent No.: US 10,429,400 B2
(45) Date of Patent: Oct. 1, 2019

(54) CHEMICAL ASSAY TO VERIFY THE QUANTITY AND QUALITY OF SESQUITERPENE LACTONE DERIVATIVES

(71) Applicants: South Dakota Board of Regents, Pierre, SD (US); Rochester Institute of Technology, Rochester, NY (US)

(72) Inventors: Daniel Heglund, Rapid City, SD (US); Andrew Olson, Lincoln, NE (US); Scott Williams, Livonia, NY (US); Neal Hodges, Rapid City, SD (US); Joseph A. Marshall, Rapid City, SD (US)

(73) Assignees: South Dakota Board of Regents, Pierre, SD (US); Rochester Institute of Technology, Rochester, NY (US)

( * ) Notice: Subject to any disclaimer, the term of this patent is extended or adjusted under 35 U.S.C. 154(b) by 73 days.

(21) Appl. No.: 15/309,293

(22) PCT Filed: May 7, 2015

(86) PCT No.: PCT/US2015/029573
§ 371 (c)(1),
(2) Date: Nov. 7, 2016

(87) PCT Pub. No.: WO2015/171839
PCT Pub. Date: Nov. 12, 2015

(65) Prior Publication Data
US 2017/0115317 A1    Apr. 27, 2017

Related U.S. Application Data

(60) Provisional application No. 61/990,186, filed on May 8, 2014.

(51) Int. Cl.
*G01N 33/94* (2006.01)
*G01N 21/78* (2006.01)
(Continued)

(52) U.S. Cl.
CPC ............. *G01N 33/94* (2013.01); *G01N 21/78* (2013.01); *G01N 31/22* (2013.01); *G01N 33/52* (2013.01); *Y02A 50/58* (2018.01)

(58) Field of Classification Search
CPC ......... G01N 21/78; G01N 33/52; G01N 33/94
See application file for complete search history.

(56) References Cited

U.S. PATENT DOCUMENTS

| 5,387,515 A * | 2/1995 | Bruce | C12N 9/0006 435/119 |
|---|---|---|---|
| 8,247,018 B2 | 8/2012 | Mercolino | |

(Continued)

FOREIGN PATENT DOCUMENTS

| WO | WO-03048766 A2 * | 6/2003 | ............. G01N 33/52 |
|---|---|---|---|
| WO | 2007077444 A1 | 7/2007 | |

OTHER PUBLICATIONS

Burke, John, "Solubility Parameters: Theory and Application," http://cool.conservation-us.org/coolaic/sg/bpg/annual/v03/bp03-04.html, Retrieved Aug. 17, 2015 (Year: 2015).*

(Continued)

*Primary Examiner* — Jennifer Wecker
(74) *Attorney, Agent, or Firm* — McKee, Voorhees & Sease, PLC

(57) ABSTRACT

The present invention relates to methods of testing medications to evaluate authenticity and identify counterfeits. The testing methods employ a reactive system comprising a solvent and an acid. Optionally, the reactive system can also comprise an organometallic agent. The testing methods can provide rapid results verifying the authenticity of an anti-malarial medication. Further the test method can provide clear results that can be implemented and interpreted without special training, anywhere in the world. The test methods can offer quantitative and qualitative results. The test methods are based on reactions that yield different colors where the color can indicate the presence of an active ingredient, and the intensity of the color can indicate the concentration of the active ingredient.

20 Claims, 1 Drawing Sheet

(51) Int. Cl.
   G01N 33/52    (2006.01)
   G01N 31/22    (2006.01)

(56)            References Cited

U.S. PATENT DOCUMENTS

| 8,435,794 | B2 | 5/2013 | Green |
| 2006/0034899 | A1* | 2/2006 | Ylitalo ............... A61L 15/46 424/448 |
| 2010/0297775 | A1* | 11/2010 | Green ............... G01N 21/29 436/93 |
| 2012/0003209 | A1* | 1/2012 | Tran ............... C12N 15/113 424/133.1 |
| 2013/0034908 | A1* | 2/2013 | Barstis ............... G01N 31/22 436/43 |

OTHER PUBLICATIONS

Abafe, et al, "Development and Validation of a Thin Layer Chromatographic Method for the Simultaneous Determination of . . . " https://www.researchgate.net/publication/263709202, article dated Jan. 2011 Jan. 31, 2011.
Adegoke, et al., "Derivatization of Artesunate and Dihydroartemisinin for Colorimetric Analysis Using . . . ", https://www.researchgate.net/publication/228518667, accessed by author on Mar. 15, 2011.
Adegoke, et al., "Derivatization of Artemisinin Derivatives Using 4-Carboxyl-2, 6-dinitro Benzenediazonium (CDNBD) Ion", Acta Pharmaceutica Sciencia, vol. 52, pp. 269-280, Accepted Oct. 20, 2009.
Agarwal, et al., "Estimation of Artemether and Arteether by High Performance Thin Layer Chromatography," Asian Journal of Chemistry, vol. 19, No. 6, pp. 4407-4414, Accepted Apr. 16, 2007.
Aldrich, Emily, Undergraduate Research Poster Abstract, American Chem Society Conference Sep. 9, 2013.
Arun, et al., "Development and Validation of Analytical Method for Artemether by HPLC," Journal article from ProQuest, Document ID: 1513241110, Mar. 15, 2017.
Bowles, et al., "Chemiluminescent Identification and Quantification of Artemisinin and Relevant Sesquiterpene Lactone Derivatives," Applied Spectroscopy, vol. 66, No. 2, Accepted Nov. 7, 2011.
Burke, John, "Solubility Parameters: Theory and Application," http://cool.conservation-us.org/coolaic/sg/bpg/annual/v03/bp03-04.html, Retrieved Aug. 17, 2015.
Debnath, et al., "Determination of the Antimalaria Drug Artemether in Pharmaceutical Preparations . . . ", http://minitex.umn.edu, Processed on Mar. 15, 2017.
Fernandex, Facundo, "Prevalence and Detection of Counterfeit Pharmaceuticals: A Mini Review", Georgia Institue of Technology, pp. 585-590 Jul. 13, 2007.
Green, Michael et al., "Use of Refractometry and Colorimetry as Field Methods to Rapidly Assess Antimalarial Drug Quality", Minitex, vol. 43, pp. 105-110 Mar. 15, 2017.
Green, Michael et al., "A Colorimetric Field Method to Access the Authenticity of Drugs Sold as the Antimalarial Artesunate", Minitex, vol. 24, pp. 65-70 Mar. 15, 2017.
South Dakota Board of Regents, PCT/US2015/029573 filed May 7, 2015, "Notification of Transmittal of the International Search Report and the Written Opinion of the International Searching Authority, or the Declaration", dated May 7, 2017.
Kaur, et al., "Antimalarial Drug Quality: Methods to Detect Suspect Drugs", Research Gate Publication Jan. 2010.
Loset J-R, et a., "Simple Field Assays to Check Quality of Current Artemisinin-Based Antimalarial Combination Formulations", Plos One, vol. 4, Issue 9 Sep. 30, 2009.
Martino, et al., "Counterfeit Drugs: Analytical Techniques for Their Identification", Springer-Verlag 2010 May 1, 2010.
Men et al., "A Simple and Inexpensive Haemozoin-Based Colorimetric Method to Evaluate Anti-Malarial Drug Activity", Malaria Journal Aug. 9, 2012.
Newton, et al., "Counterfeit Anti-Infective Drugs", vol. 6, pp. 602-613 Mar. 16, 2017.
Okwelogu, et al., "Development of a Simple UV Assay Method for Artesunate in Pharmaceutical Formulations", Journal of Chemical and Pharmaceutical Research, pp. 277-285 Jan. 2011.
Rodomonte et al., "Journal of Pharmaceutical and Biomedical Analysis", vol. 53, pp. 215-220 Mar. 15, 2017.
Saini, et al., "A Simple and Sensitive HPTLC Method for Quantitative Analysis of Artemether and Lumefantrine in Tablets", Journal of Planar Chromatography May 3, 2010.
Sreevidya et al., "A Simple and Rapid Spectrophotometric Method for the Determination of Artesunate in Pharmaceuticals", Research Gate Jan. 2009.
Harwood, et al., "Colorimetric Determination of Antimalarial Combination Therapies", Undergraduate Research Poster Session Mar. 26, 2012.
Virupaxappa, et al., "Spectrophtometric Method for the Determination of Artenimol Using Rhodamine B as a New Reagent", Journal of Chemical and Pharmaceutical Research, pp. 1822-1826 2012.
Olsen, et al., "Authentication and Fingerprinting of Suspect Counterfeit Drugs", Lilly Research Laboratories Jan. 2006.
Newton, et al., "Murder by Fake Drugs", Tropical Medicine and Infectious Disease Apr. 6, 2002.

* cited by examiner

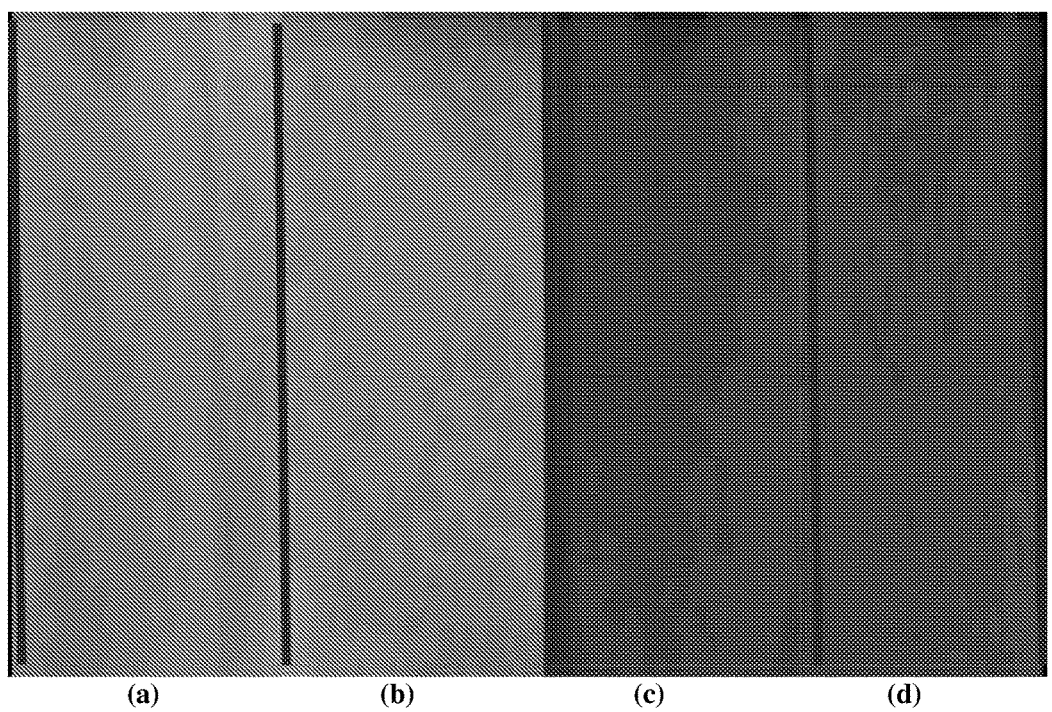

CHEMICAL ASSAY TO VERIFY THE QUANTITY AND QUALITY OF SESQUITERPENE LACTONE DERIVATIVES

CROSS-REFERENCE TO RELATED APPLICATIONS

This is a National Phase Application under 35 U.S.C. § 371 of PCT/US/2015/029573 filed on May 7, 2015, which claims priority under 35 U.S.C. § 119 to provisional application Ser. No. 61/990,186, filed May 8, 2014, which is hereby incorporated by reference in its entirety.

FIELD OF THE INVENTION

The invention relates to testing methods and kits for authenticating medications and/or quantifying the active ingredients. In particular, the invention relates to testing methods and kits for authenticating antimalarial medications and/or quantifying the active ingredients, namely sesquiterpene lactone derivatives.

BACKGROUND OF THE INVENTION

Many common medications are counterfeited annually and could benefit from a simple means of verifying authenticity. It was estimated that on an annual basis consumers in western European countries spend at least $14 billion (USD) on counterfeit medications. Worldwide, counterfeit medications sold were estimate to reach about $75 billion (USD) in 2010. The counterfeit medications include drugs intended to treat *Plasmodium falciparum* (malaria), erectile dysfunction, obesity, influenza and other illnesses or conditions. Malaria infects between 200 and 500 million people per year worldwide. Nearly one million deaths per year occur, mostly in children five years old and younger, due to malaria. Fortunately, there is an effective therapy that is successful at treating the malaria. Unfortunately, many of the antimalarial medications delivered to patients are counterfeit. The World Health Organization found that in 2011 64% of antimalarial drugs were counterfeit. Often, the counterfeit manufacturers duplicate the pills so that they appear identical in color, shape, size, demarcation, blister packaging, etc. In some instances, the counterfeit medication contains no active ingredients with efficacy against malaria. These counterfeits can be any chemical agent that has a physical appearance similar to the active malaria drug, but has no pharmaceutical activity toward the disease. Non-limiting examples of these counterfeit agents include, but are not limited to, aspirin, acetaminophen, NSAIDs, vitamins, starch, cellulose, caffeine and other inert powdered agents. More sophisticated counterfeit medications can include a small amount of the active ingredient so that the medication satisfies qualitative testing. In such an instance, the medication will test positive for the presence of the active antimalarial ingredient, but it is not provided in an amount sufficient to be efficacious. Previously, it was found that certain antimalarial medications could be identified through colorimetric tests (U.S. Pat. No. 8,435,794); however, these methods and tests took an excessive amount of time—greater than 30 minutes to provide a discernable difference in color at 20° C. It was found the speed of the reaction could be increased under a temperature control of 40° C. However, this is undesirable as it would require temperature controlled parameters on the use of method. Thus, the amount of time required near room temperature or the need for a temperature controlled test made this colorimetric method impractical and ultimately undesirable. Thus, there is an immediate need to develop technologies and methods for authenticating malaria medications in a time quickly enough for necessary end use and that can be performed at room temperature. Further, there is a need for a testing method that not only provides qualitative results but also quantitative results.

Accordingly, it is an object of the present invention to provide technology and/or methods for identifying and authenticating malaria medications.

It is a further object of the present invention to provide technology and/or methods for identifying and authenticating malaria medications at room temperature.

It is still a further object of the present invention to provide technology and/or methods for identifying counterfeit medication, in particular, counterfeit malaria medication.

It is a further object of the present invention to provide technology and methods to provide rapid results in a matter of minutes.

It is yet a further object of the invention to provide technology and methods for quantifying the amount of active medication in a drug.

BRIEF SUMMARY OF THE INVENTION

The present invention relates to methods of testing medications to evaluate authenticity. The testing methods employ a reactive system comprising a solvent and an acid. Optionally, the reactive system can also comprise an organometallic agent. The testing methods can provide rapid results verifying the authenticity of a antimalarial medication. Further the test method provides clear results that can be implemented and interpreted without special training, anywhere in the world. The test methods can provide quantitative and qualitative results. The test methods are based on reactions that yield different colors where the color can indicate the presence of an active ingredient, and the intensity of the color can indicate the concentration of the active ingredient.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE FIGURES

FIG. 1 shows four photographs demonstrating the quantitative results of the testing methods employing the reactive system by verifying the presence of the artemether in the amounts of (a) 5 mg, (b) 10 mg, (c) 20 mg, and (d) 30 mg.

Various embodiments of the present invention are described in detail with reference to the figures. The reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENTS

The present invention relates to testing methods and kits for authenticating medications and/or quantifying the active ingredients. The testing methods and kits of the present invention have many advantages over existing technology.

For example, the testing methods and kits of the present invention provide unmistakably clear results that can be implemented and interpreted without special training, anywhere in the world. The testing methods and kits of the present invention offer both quantitative and qualitative results. The testing methods and kits of the present invention yield different colors where the actual color indicates the presence of the active ingredient, and the intensity of the color indicates the concentration of the active ingredient. The testing methods and kits of the present invention test are very inexpensive to produce, manufacture, and employ. The testing methods and kits of the present invention provide rapid results, on the order of minutes.

The embodiments of this invention are not limited to particular test kits or medications, in particular, antimalarial medications, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range.

The term "about," as used herein, modifying the quantity of an ingredient in the compositions of the invention or employed in the methods of the invention refers to variation in the numerical quantity that can occur, for example, through typical measuring and liquid handling procedures used for making concentrates or use solutions; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about," the claims include equivalents to the quantities. All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers subsumed within that range (e.g., 1 to 5 includes 1, 1.5, 2, 2.75, 3, 3.80, 4, and 5).

Reactive System

The invention employs a reactive system providing colorimetric reactions for examining both the quality and quantity of active sesquiterpene lactone ingredients in antimalarial medications, including, but not limited to, artemisinin, artesunate, artemether, arteether, and dihydroartemisinin. The testing methods provide a reactive system that employs a solvent for reacting with a medication in a solution-based reactive system. The medication can be in any form, e.g., injectable liquid, orally administered liquid, gel cap, pill, etc. In an embodiment of the invention, the solvent is intended to react with sesquiterpene lactone derivatives, which are commonly an active ingredient in antimalarial medications. The reagent provides an unexpected reaction with sesquiterpene lactone derivatives. This unexpected reaction with sesquiterpene lactone derivatives results in color changes in both hue and intensity. Thus, it is a color positive test and can be used to provide a testing method for authenticating the presence of sesquiterpene lactone derivatives in antimalarial medications. Further, because the reaction results in color changes in both hue and intensity, the testing methods can also assist with quantification of the active ingredient(s) (sesquiterpene lactone derivative(s)) to ensure the medication is not counterfeit with a diluted amount of active ingredient. When a counterfeit medicine is encountered that does not contain any active ingredient then, the test will result in no color change. If the medication contains an active antimalarial ingredient, then the color will change to a hue associated with the specific active ingredient and an intensity associated with an amount of the active ingredient.

Solvent

The reactive system comprises a solvent. The solvent is not a passive solvent medium, but is reactive and participates in the color forming reaction. Preferably the solvent is colorless or slightly tinted. Preferably the solvent has a Hildebrand solubility of about less than 28 $MPa^{1/2}$, preferably between 8 and 26 $MPa^{1/2}$, and most preferably between 15 to 22 $MPa^{1/2}$.

The solvent can include, but is not limited to, one or more short chain esters containing between 1 and 20 carbon atoms, one or more alcohols containing between 1 and 12 carbon atoms, one or more aldehydes containing between 1 and 20 carbon atoms, one or more short chain organic acids containing between 1 and 6 carbon atoms, one or more long chain organic acids containing between 7 and 12 carbon atoms, and mixtures thereof. Preferred solvents include allyl hexonate, benzyl acetate, butyl acetate, butyl butyrate, butyl propanoate, ethyl acetate, ethyl lactate, ethyl butyrate, ethyl hexanoate, ethyl cinnamate, ethyl formate, ethyl heptanoate, ethyl isovalerate, ethyl nonanoate, ethyl pentanoate, isobutyl acetate, isobutyl formate, isoamyl acetate, methyl benzoate, methyl cinnamate, methyl pentanoate, octyl acetate, octyl butyrate, amyl acetate, pentyl butyrate, pentyl hexonoate, propyl lactate, butyl lactate, ethanol, propanol, butanol, t-butanol, sec-butanol, and mixtures thereof.

The solvent can be added to the reactive system in an amount between about 0.01 milliliters and about 5.0 milliliters; preferably between about 1 milliliters and about 4 milliliters; and most preferably between about 2 milliliters and about 3 milliliters.

Acid

The reactive system comprises an acid. The acid participates in the color forming reaction. Preferably the acid is a protic acid with an aqueous pKa of less than about 4.75, preferably less than 2, most preferably less than zero. The pKa of the acid may vary in organic solvents, and so they are described based on their aqueous dissociation behavior. Strong protic acids, such as sulfuric acid, have a pKa of less than zero indicating nearly complete dissociation in water.

Suitable acids include, but are not limited to, hydrobromic acid, hydrochloric acid, perchloric acid, hydrofluoric acid, sulfurous acid, sulfuric acid, hydrazoic acid, nitric acid, nitrous acid, phosphoric acid, chromic acid, methansulfonic acid, trifluoromethanesulfonic acid, and mixtures thereof. Preferred acids include, but are not limited to, hydrobromic acid, hydrochloric acid, perchloric acid, sulfurous acid, sulfuric acid, nitric acid, methanesulfonic acid, trifluoromethanesulfonic acid, and mixtures thereof. Most preferred acids include, but are not limited to, hydrochloric acid and sulfuric acid.

The acid can be added to the reactive system in an amount between about 0.001 milliliters and about 2 milliliters;

preferably between about 0.1 milliliters and about 1.5 milliliters; and most preferably between about 0.5 milliliters and about 1.0 milliliters. The acid can be added to reactive system a liquid or as a gas bubbled into the reactive system.

Organometallic Agent

Optionally, the reactive system can comprise an organometallic agent. The organometallic agent can be selected based on the identity of the acid and solvent to provide specific color hues (for example, indigo or red) when the reactive system is combined with a sesquiterpene lactone derivative. Preferably the organometallic agent comprises one or more transition metals. Preferred transition metals include, but not limited to, iron, cobalt, zinc, nickel, manganese, chromium, copper, silver, platinum, ruthenium and gold in their neutral, partial or fully oxidized state. Organometallic complexes with iron (II) ion are most preferred. Transition metal salts can be selected from any compound whereby the metal is complexed with the appropriate stoichiometric amount of a counter anion, or complex ions of, those selected from Group IV-VII atoms. Preferred counter anions include, but are not limited to, halogens, sulfates, sulfites, nitrates, nitrites, phosphates, phosphites, and combinations thereof. Preferably the organometallic agent comprises transition metal ion complex with aliphatic and/or aromatic organic molecules. Exemplary organometallic agents include, but are not limited to, metal alkoxides, carbonyls, peralkyls, peraryls, and polyhapto complexes.

Preferred organometallic agents, include, but are not limited to, ferrocene, ferrocene derivatives, iron (II) chloride, iron (III) chloride, iron (II) sulfate, ferric ammonium sulfate dodecahydrate, and combinations thereof. Most preferred organometallic agents are ferrocene and ferrocene derivatives, including, but not limited to, decamethylferrocene, methyl ferrocenylacetate, ferrocenylacetic acid, 1,1'-diethylferrocene.

The optional organometallic agent can be added to the reactive system in an amount an amount effective to provide the desired color enhancement or change. Typically, the optional organometallic agent can be included in the reactive system in an amount between about 0.0001 and about 0.100 grams; preferably between about 0.0005 and about 0.015 grams; and most preferably between about 0.0010 and about 0.010 grams. The organometallic agent can be added in the form of a salt or salt solution.

Additional Components

Additional components can be added to the reactive system to alter the resulting color positive result. These additional components include, but are not limited to, one or more color changing additives, one or more polar solvents, one or more sugars, one or more carbohydrates, one or more organic acids, one or more aldehydes, one or more organic bases, and one or more miscible organic solvents. These color changing additives may include, but not limited to water, ethanol, pyridine, ethyl acetate, linoleic acid, benzaldehyde, vanillin, cinnamon, lactic acid, sucralose (1,6-Dichloro-1,6-dideoxy-β-D-fructofuranosyl-4-chloro-4-deoxy-α-D-galactopyranoside), starch, hydrogen peroxide, luminol, and hematin.

The color formed, using the invention, can be designed to produce a plurality of color results depending on the combination of time, temperature, acid, solvent, and optional organometallic agent and/or additional component. Colors formed can be designed to match the maximum sensitivity of the human photopic color visual perception range for the standard observer. These colors include, but not limited to shades of red, orange, yellow, green, blue, indigo, and violet. The resulting chroma, hue, and intensity of each color test can be designed to vary by only about 20 delta E units, preferably 10 delta E units, and most preferably 5 delta E units (according to the CIElab delta E 2000 specifications).

Testing Methods

The testing methods comprise combining a reactive system and a medication. If the medication is in a pill form, it should be crushed so that its ingredients are exposed. This can be done by any method such as a pill crusher, mortar and pestle, pinching device, etc. A preferred method is by using a pill crushing apparatus. If the medication is a gel cap, the gel cap can be opened to facilitate removal of the liquid medication. The reactive system and exposed ingredients of the medication are combined and allowed to react. The medication can be added to the reactive system (for example, by adding part of a crushed pill to the reactive system), or the reactive system can be added to the medication (for example, by dropwise addition). In a preferred embodiment, the reactive system is contained in an ampule that is ruptured and combined with the exposed ingredients of a medication.

Optionally, the mixture of the reactive system and medication can be filtered. Sufficient time for the reactive system and ingredients in the medication to react can be provided such that the desired color forming reaction is completed. At a temperature of about 20° C., the elapsed time is less than 30 minutes, preferably from about 30 seconds to about 25 minutes, more preferably from about 1 minute to about 20 minutes, even more preferably from about 2 minutes to 15 minutes, and most preferably between about 3 minutes and 5 minutes. The reaction temperature may vary from 20° C. to 40° C., preferably 20-35° C. and most preferably 20 to 30° C. After the reactive system has reacted with the medication a color will become apparent. The color can indicate the presence of particular active ingredients (qualitative) and the intensity can indicate how much of that ingredient is present (quantitative). To facilitate quantitative analysis a color comparison chart can be provided to compare the mixed reactive system and medication quantify the amount of active ingredient present in the medication.

Test Kits

Test kits can be prepared that contain a color comparison chart, ampules of the reactive system, a pill crusher, and optionally a container to mix the medication and reactive system in. The procedure for using such a test kit is simple. A suspect medication can be added to container and combined with the reactive system. If the medication is in pill form, the medication can be crushed with a pill crusher, add the contents of an ampule and wait for the color to develop. If the color of the liquid matches the chart, the pill contains the active ingredient at the indicated dose. If the color does not match the comparison chart, the pill is suspect.

In another embodiment of the invention, the reactive system can be provided in a container and removed by a dropper or pipette as opposed to an ampule. Further, kits can be provided that include the solvent, acid, and optional ingredients in separate containers. Each component can be then be added together at the time of use to provide the reactive system.

In embodiments of the invention, the reactive system is shelf-stable and has a storage life of at least 3 months, preferably at least 6 month, more preferably at least one year.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example I

To demonstrate the quantitative nature of the testing methods, 5, 10, 20 and 30 mg of artemether was reacted separately with a reactive system of ethyl lactate and HCl the results are shown in FIG. 1. FIG. 1(a) shows the sample with 5 mg of artemether, which appeared a pale yellow. FIG. 1(b) shows the sample with 10 mg of artemether, which appeared a tanish yellow. FIG. 1(c) shows the sample with 20 mg of artemether, which appeared a moss green. FIG. 1(d) shows the sample with 30 mg of artemether, which appeared green.

Example II

The shelf-life of the reactive system was tested. To test the shelf-life of the reactive system ampules, several ampules containing the reactive system were created at the same time and sealed. Every week for six weeks, the contents of an ampule was added to 20 mg of artemether and tested. There was little, if any, color variation over the six week span. Thus, the reactive system was found to be efficacious after storage for at least 6 weeks.

Additional shelf-life tests were performed at different time intervals up to a year in duration. Again there was little, if any, difference in color intensity. Thus, the reactive system was found to be shelf-stable for period of at least one year in a sealed container.

Example III

Various exemplary reactive systems were tested. The following examples provide exemplary tested reactive systems and methods relating to the same. All of the tests in the following examples were efficacious and capable of authenticating the presence of active antimalarial medications and thereby providing results that differentiate between bona fide medications and counterfeit medications. Further, the examples demonstrate the ability for the test methods and reactive system to provide quantitative results. The examples tested ranges of ingredients in the reactive system, various quantities of active ingredients, and ranges of other factors, including, for example, temperature. While not being limiting, the preferred values are also provided.

Example A

| | |
|---|---|
| 5-30 mg | Artemisinin, Artesunate, Dihydroartemisinin or Artemether 20 mg most preferred |
| 0.5-5 ml | Ethyl Lactate 3 ml most preferred |
| 0-40 mg | 1,6-Dichloro-1,6-dideoxy-β-D-fructofuranosyl-4-chloro-4-deoxy-α-D-galactopyranoside 10 mg most preferred |
| 45-250 mg | Aluminum Chloride 180 mg most preferred |
| 0.5-5 minutes | 3 minutes most preferred |
| 10-100° C. | 58° C. most preferred |

Example B

| | |
|---|---|
| 5-30 mg | Artemisinin, Artesunate, Dihydroartemisinin or Artemether 20 mg most preferred |
| 0.5-5 ml | Ethyl Lactate 3 ml most preferred |
| 0-40 mg | 1,6-Dichloro-1,6-dideoxy-β-D-fructofuranosyl-4-chloro-4-deoxy-α-D-galactopyranoside 10 mg most preferred |
| 0.1-5 ml | concentrated HCl; 0.75 ml most preferred |
| 0.5-5 minutes | 3 minutes most preferred |
| 10-100° C. | 58° C. most preferred |

Example C

Reaction Using Example A
Adding 10-1000 µl of distilled water; 60 µl most preferred

Example D

Reaction Using Example B
Adding 10-1000 µl of distilled water; 60 µl most preferred

Example E

| | |
|---|---|
| 5-30 mg | Artemisinin, Artesunate, Dihydroartemisinin or Artemether 20 mg most preferred |
| 0.5-5 ml | Ethyl Lactate 3 ml most preferred |
| 0-40 mg | 1,6-Dichloro-1,6-dideoxy-β-D-fructofuranosyl-4-chloro-4-deoxy-α-D-galactopyranoside 10 mg most preferred |
| 0.1-3 ml | Concentrated HCl gas added by bubbling 2.5 ml most preferred |
| 0.5-5 minutes | 3 minutes most preferred |
| 10-100° C. | 58° C. most preferred |

Example F

Reaction Using Example E
10-1000 µL of distilled water added; 60 µL is most preferred.

Example G

| | |
|---|---|
| 5-30 mg | Artemisinin, Artesunate, Dihydroartemisinin or Artemether 20 mg most preferred |
| 0.5-5 ml | Ethyl Lactate 3 ml most preferred |
| 0-40 mg | 1,6-Dichloro-1,6-dideoxy-β-D-fructofuranosyl-4-chloro-4-deoxy-α-D-galactopyranoside 10 mg most preferred |

-continued

| | |
|---|---|
| 0.1-5 ml | 6-12M HCl |
| | 0.75 ml most preferred; 12M HCl most preferred |
| 0.5-5 minutes | 3 minutes most preferred |
| 10-100° C. | 25° C. most preferred |

Example H

| | |
|---|---|
| 5-30 mg | Artemisinin, Artesunate, Dihydroartemisinin or Artemether 20 mg most preferred |
| 0.5-5 ml | Ethyl Lactate |
| | 3 ml most preferred |
| 0.1-5 ml | 6-12M HCl |
| | 0.75 ml most preferred; 12M HCl most preferred |
| 0.5-5 minutes | 3 minutes most preferred |
| 10-100° C. | 25° C. most preferred |

Example I

| | |
|---|---|
| 5-30 mg | Artemisinin, Artesunate, Dihydroartemisinin or Artemether 20 mg most preferred |
| 0.5-5 ml | Ethyl Lactate |
| | 3 ml most preferred |
| 0.001-0.150 ml | distilled Water |
| | 0.01 ml most preferred |
| 0.1 to 5 ml | 6-12M HCl |
| | 0.75 ml most preferred; 12M HCl most preferred |
| 0.5-5 minutes | 3 minutes most preferred |
| 10-100° C. | 25° C. most preferred |

Example J

| | |
|---|---|
| 5-30 mg | Artemisinin, Artesunate, Dihydroartemisinin or Artemether 20 mg most preferred |
| 0.5-5 ml | Ethyl Lactate |
| | 3 ml most preferred |
| 0.1-100 mg | Ferrocene |
| | 1 mg most preferred |
| 0.1 to 5 ml | 6-12M HCl |
| | 0.75 ml most preferred; 12M HCl most preferred |
| 0.5-5 minutes | 3 minutes most preferred |
| 10-100° C. | 25° C. most preferred |

Example K

| | |
|---|---|
| 5-30 mg | Artemisinin, Artesunate, Dihydroartemisinin or Artemether 20 mg most preferred |
| 0.5-5 ml | Ethyl Lactate |
| | 3 ml most preferred |
| 0.1-100 mg | Ferrocenylacetic acid |
| | 1 mg most preferred |
| 0.1-5 ml | 6-12M HCl |
| | 0.75 ml most preferred; 12M HCl most preferred |
| 0.5-5 minutes | 3 minutes most preferred |
| 10-100° C. | 25° C. most preferred |

Example L

| | |
|---|---|
| 5-30 mg | Artemisinin, Artesunate, Dihydroartemisinin or Artemether 20 mg most preferred |
| 0.5-5 ml | Ethyl Lactate |
| | 3 ml most preferred |
| 0.1-100 mg | 1,1'-Diethylferrocene |
| | 1 mg most preferred |
| 0.1-5 ml | 6-12M HCl |
| | 0.75 ml most preferred; 12M HCl most preferred |
| 0.5-5 minutes | 3 minutes most preferred |
| 10-100° C. | 25° C. most preferred |

Example M

| | |
|---|---|
| 5-30 mg | Artemisinin, Artesunate, Dihydroartemisinin or Artemether 20 mg most preferred |
| 0.5-5 ml | Ethyl Lactate |
| | 3 ml most preferred |
| 0.1-100 mg | Decamethylferrocene |
| | 1 mg most preferred |
| 0.1-5 ml | 6-12M HCl |
| | 0.75 ml most preferred; 12M HCl most preferred |
| 0.5-5 minutes | 3 minutes most preferred |
| 10-100° C. | 25° C. most preferred |

Example N

| | |
|---|---|
| 5-30 mg | Artemisinin, Artesunate, Dihydroartemisinin or Artemether 20 mg most preferred |
| 0.5-5 ml | Ethyl Lactate |
| | 3 ml most preferred |
| 0.1-100 mg | Methyl Ferrocenylacetate |
| | 1 mg most preferred |
| 0.1-5 ml | 6-12M HCl |
| | 0.75 ml most preferred; 12M HCl most preferred |
| 0.5-5 minutes | 3 minutes most preferred |
| 10-100° C. | 25° C. most preferred |

Example O

| | |
|---|---|
| 5-30 mg | Artemisinin, Artesunate, Dihydroartemisinin or Artemether 20 mg most preferred |
| 0.5-5 ml | Ethyl Lactate |
| | 3 ml most preferred |
| 0.1-100 mg | Iron (II) Chloride |
| | 10 mg most preferred |
| 0.1-5 ml | 6-12M HCl |
| | 0.75 ml most preferred; 12M HCl most preferred |
| 0.5-5 minutes | 3 minutes most preferred |
| 10-100° C. | 25° C. most preferred |

Example P

| | |
|---|---|
| 5-30 mg | Artemisinin, Artesunate, Dihydroartemisinin or Artemether 20 mg most preferred |
| 0.5-5 ml | Ethyl Lactate |
| | 3 ml most preferred |
| 0.1-100 mg | Ferric Ammonium Sulfate dodecahydrate |
| | 10 mg most preferred |

Example Q

| | |
|---|---|
| 5-30 mg | Artemisinin, Artesunate, Dihydroartemisinin or Artemether 20 mg most preferred |
| 0.5-5 ml | Ethyl Lactate<br>3 ml most preferred |
| 0.1-100 mg | Iron (III) chloride<br>1 mg most preferred |
| 0.1-5 ml | 6-12M HCl<br>0.75 ml most preferred; 12M HCl most preferred |
| 0.5-5 minutes | 3 minutes most preferred |
| 10-100° C. | 25° C. most preferred |

Example R

| | |
|---|---|
| 5-30 mg | Artemisinin, Artesunate, Dihydroartemisinin or Artemether 20 mg most preferred |
| 0.5-5 ml | Ethyl Lactate<br>3 ml most preferred |
| 0.1-100 mg | Iron (II) Sulfate<br>10 mg most preferred |
| 0.1-5 ml | 6-12M HCl<br>0.75 ml most preferred; 12M HCl most preferred |
| 0.5-5 minutes | 3 minutes most preferred |
| 10-100° C. | 25° C. most preferred |

Example S

Examples A-R were performed but substituting the active sesquiterpene lactone ingredient with a known counterfeit; example Excedrin. The methods of Examples A-R were successful in identifying the known counterfeit by not reacting.

Example T

Examples A-R were performed where the active sesquiterpene lactone ingredient is obtained by crushing a pill and extracting the active ingredient in ethyl lactate then separating the binder from the extract by filtration. The methods of Examples A-R were successful in identifying the active sesquiterpene lactone ingredient by reacting and providing the desired color.

Example U

Examples A-R were performed where the active sesquiterpene lactone ingredient is obtained by crushing a pill and conducting the test by directly using the crushed product (unfiltered). The methods of Examples A-R were successful in identifying the active sesquiterpene lactone ingredient by reacting and providing the desired color.

The above specification provides a description of the manufacture and use of the disclosed compositions and methods. Since many embodiments can be made without departing from the spirit and scope of the invention, the invention resides in the claims.

What is claimed is:

1. A method for authenticating a medication comprising:
   obtaining an antimalarial medication;
   combining a reactive system and the antimalarial medication, wherein the reactive system comprises a solvent comprising ethyl lactate, and an acid, wherein the solvent has a Hildebrand solubility of less than 24 MPa$^{1/2}$; and wherein the acid has a pKa of less than 4.75;
   allowing the reactive system and the antimalarial medication to react for less than 30 minutes at a temperature of between about 20° C. to about 35° C.; wherein the solvent reacts with the antimalarial medication to produce a color change; and
   identifying whether the antimalarial medication is counterfeit or efficacious based on the color change.

2. The method of claim 1 wherein the antimalarial medication comprises one or more of artemisinin, artesunate, artemether, arteether, and dihydroartemisinin.

3. The method of claim 1, further comprising quantifying the efficacious medication.

4. The method of claim 1 wherein the medication is a solid pill, and the method further comprises crushing the solid pill to expose an active ingredient, and wherein said combining step is combining the reactive system and the exposed active ingredient.

5. The method of claim 1 wherein the ethyl lactate is present in the amount of about 0.01 mL to about 5 mL.

6. The method of claim 1 wherein the reactive system further comprises an organometallic agent.

7. The method of claim 6 wherein the organometallic agent is selected from the group consisting of ferrocene, ferrocene derivatives, iron (II) chloride, iron (III) chloride, iron (II) sulfate, ferric ammonium sulfate dodecahydrate, and combinations thereof.

8. The method of claim 3 wherein the reactive system and the medication are allowed to react for a time between 30 seconds and 25 minutes at a temperature between about 20° C. to about 30° C.

9. The method of claim 1 wherein the reactive system further comprises at least one of the following additional components: one or more color changing additives, one or more polar solvents, one or more sugars, one or more carbohydrates, one or more organic acids, one or more aldehydes, one or more organic bases, and one or more miscible organic solvents.

10. A reactive system for authenticating a medication comprising:
    a solvent comprising ethyl lactate, wherein the solvent has a Hildebrand solubility of less than 24 MPa$^{1/2}$; and
    an acid, wherein the acid has a pKa of less than 4.75;
    wherein the solvent reacts with an antimalarial medication to produce a color change.

11. The system of claim 10 wherein the solvent is further selected from the group consisting of a short chain ester, an alcohol, an aldehyde, a short chain organic acid, and a long chain organic acid, and mixtures thereof.

12. The system of claim 10 wherein the acid has a pKa of less than 2.

13. The system of claim 10 wherein the acid is selected from the group consisting of bromic acid, hydrochloric acid, perchloric acid, hydrofluoric acid, sulfurous acid, sulfuric acid, hydrazoic acid, nitric acid, nitrous acid, phosphoric acid, chromic acid, methansulfonic acid, trifluoromethanesulfonic acid, and mixtures thereof.

14. The system of claim 10 further comprising an organometallic agent.

15. The system of claim 14 wherein the organometallic agent is selected from the group consisting of ferrocene, ferrocene derivatives, iron (II) chloride, iron (III) chloride, iron (II) sulfate, ferric ammonium sulfate dodecahydrate, and combinations thereof.

16. The system of claim 10 further comprising at least one of the following additional components: one or more color changing additives, one or more polar solvents, one or more sugars, one or more carbohydrates, one or more organic acids, one or more aldehydes, one or more organic bases, and one or more miscible organic solvents.

17. The system of claim 14, wherein the acid comprises hydrochloric acid or sulfuric acid, and the organometallic agent comprises iron.

18. A kit for identifying whether a medication is counterfeit comprising:
a reactive system comprising a solvent comprising ethyl lactate, and an acid, wherein the solvent has a Hildebrand solubility of less than 24 $MPa^{1/2}$; and wherein the acid has a pKa of less than 4.75;
a container for mixing the reactive solvent with an antimalarial medication;
optionally a pill crusher; and
optionally a color chart;
wherein the solvent reacts with the antimalarial medication to produce a color change.

19. The kit of claim 18 wherein the reactive system further comprises an organometallic agent.

20. The kit of claim 18 wherein the reactive system further comprises at least one of the following additional components: one or more color changing additives, one or more polar solvents, one or more sugars, one or more carbohydrates, one or more organic acids, one or more aldehydes, one or more organic bases, and one or more miscible organic solvents.

* * * * *